(12) United States Patent
Lormand-Koch

(10) Patent No.: US 9,668,909 B1
(45) Date of Patent: Jun. 6, 2017

(54) METHOD OF USING GASTROJEJUNOSTOMY DRAINAGE BAG

(71) Applicant: Ann M. Lormand-Koch, Wonder Lake, IL (US)

(72) Inventor: Ann M. Lormand-Koch, Wonder Lake, IL (US)

(*) Notice: Subject to any disclaimer, the term of this patent is extended or adjusted under 35 U.S.C. 154(b) by 215 days.

(21) Appl. No.: 13/781,184

(22) Filed: Feb. 28, 2013

Related U.S. Application Data

(63) Continuation of application No. 13/035,985, filed on Feb. 27, 2011, now abandoned.

(51) Int. Cl.
| | | |
|---|---|---|
| *A61F 5/44* | (2006.01) | |
| *A61J 15/00* | (2006.01) | |
| *A61B 5/20* | (2006.01) | |

(52) U.S. Cl.
CPC ............ *A61F 5/4407* (2013.01); *A61B 5/20* (2013.01); *A61J 15/0007* (2013.01); *A61J 15/0042* (2013.01); *A61J 15/0065* (2013.01); *A61J 15/0069* (2013.01)

(58) Field of Classification Search
USPC ................................ 604/227, 317, 318, 541
See application file for complete search history.

(56) References Cited

U.S. PATENT DOCUMENTS

| | | | | | |
|---|---|---|---|---|---|
| 3,529,599 | A | * | 9/1970 | Folkman ................ | A61F 5/441 604/323 |
| 3,683,894 | A | * | 8/1972 | Villari .................... | A61B 5/208 600/580 |
| 3,788,374 | A | * | 1/1974 | Saijo ..................... | A61J 1/10 383/207 |
| 3,906,935 | A | * | 9/1975 | Raia ...................... | A61B 5/20 128/DIG. 24 |
| 4,005,739 | A | * | 2/1977 | Winchell .............. | A61J 1/1412 383/42 |
| 4,126,167 | A | * | 11/1978 | Smith ................... | A61M 1/0019 220/375 |
| 4,335,770 | A | * | 6/1982 | Kulle .................... | A61J 1/10 220/375 |
| 4,356,824 | A | * | 11/1982 | Vazquez ............... | A61J 15/0015 604/119 |
| 4,642,105 | A | * | 2/1987 | Toter .................... | A61M 1/0019 604/323 |

(Continued)

*Primary Examiner* — Tatyana Zalukaeva
*Assistant Examiner* — Guy K Townsend
(74) *Attorney, Agent, or Firm* — Perkins Coie LLP

(57) ABSTRACT

A gastrojejunostomy tube is used when a patient's stomach must be bypassed, with nutrients and/or medication being delivered directly to the jejunum. In this situation, the stomach commonly fills with stomach acid and digestive enzymes, which may cause vomiting, acid reflux or other esophageal problems. The gastrojejunostomy drainage bag is provided to allow the contents of the stomach to be drained through the gastrojejunostomy tube, rather than building up within the patient's stomach. The gastrojejunostomy drainage bag includes a receptacle having a lower portion and an upper stem portion, the upper stem portion terminating in a port adapted for connection to the gastrojejunostomy tube. Preferably, a lower port is formed through the lower portion, allowing the contents of the gastrojejunostomy drainage bag to be selectively emptied. A method of releasing gas or trapped air from the stomach is also disclosed.

17 Claims, 3 Drawing Sheets

(56) References Cited

U.S. PATENT DOCUMENTS

| | | | | |
|---|---|---|---|---|
| 5,314,473 A * | 5/1994 | Godin | A61F 2/04 623/23.68 |
| 5,344,107 A * | 9/1994 | Lee | F16L 3/233 24/298 |
| 6,419,670 B1 * | 7/2002 | Dikeman | A61J 15/0015 604/533 |
| 7,462,171 B2 * | 12/2008 | Salvadori | A61F 5/4405 604/317 |
| 7,637,905 B2 * | 12/2009 | Saadat | A61B 1/0055 600/104 |
| 7,645,968 B2 * | 1/2010 | Salvadori | A61F 5/44 156/272.2 |
| 8,540,621 B2 * | 9/2013 | Barlow | A61B 17/12099 600/104 |
| 8,617,100 B2 * | 12/2013 | Eini | A61M 31/00 604/275 |
| 2003/0225369 A1 * | 12/2003 | McMichael | A61J 15/0015 604/104 |
| 2003/0225392 A1 * | 12/2003 | McMichael | A61J 15/0042 604/509 |
| 2003/0225393 A1 * | 12/2003 | McMichael | A61J 15/0023 604/513 |
| 2004/0249367 A1 * | 12/2004 | Saadat | A61B 1/0055 606/1 |
| 2007/0265600 A1 * | 11/2007 | Barlow | A61B 17/12099 606/1 |
| 2009/0182264 A1 * | 7/2009 | Eike | A61J 15/0015 604/28 |
| 2010/0187285 A1 * | 7/2010 | Harris | A61B 17/064 227/179.1 |
| 2010/0191258 A1 * | 7/2010 | Harris | A61B 17/0644 606/144 |
| 2011/0066254 A1 * | 3/2011 | Forsell | A61M 1/1068 623/23.64 |
| 2014/0156024 A1 * | 6/2014 | Forsell | A61F 2/04 623/23.65 |

* cited by examiner

METHOD OF USING GASTROJEJUNOSTOMY DRAINAGE BAG

This is a continuation application of U.S. patent application Ser. No. 13/035,985 filed on Feb. 27, 2011, which is entitled, "Gastojejunostomy Drainage Bag."

BACKGROUND

Field

The present invention relates to medical devices, and more particularly, to a gastrojejunostomy bag that provides for the drainage of the contents of a patient's stomach into an external drainage bag.

Description of the Related Art

Gastrostomy tubes are surgical tubes that are implanted, or placed laproscopically, in a patient. Gastrostomy tubes are typically held in place by a plastic bulb or water filled balloon, positioned within the stomach, against the stomach wall, and with a crossbar, clamp or disc on the exterior of the patient's abdomen. FIG. 2 illustrates a typical gastrostomy tube 100, with a balloon 102 mounted on one end of central tube 104. The balloon 102 is positioned within the patient's stomach, against the stomach wall. The interior-side open end 110 of central tube 104 is positioned so as to form an opening through balloon 102, opposite the anchoring surface thereof (which contacts the stomach wall), as shown.

The opposite end of central tube 104 terminates in a port 106, which is covered by a releasable cover 108. FIG. 3 illustrates the anchoring mechanism (commonly referred to as a "button") implanted within a patient, with the port 106 projecting from the patient's abdomen A. A gastrojejunostomy tube (also sometimes referred to as a percutaneous endoscopic jejunostomy tube) is used when the patient's stomach must be bypassed for dietary reasons or dysmotility. In such a situation, a smaller tube is placed through an existing gastrostomy line and clamped in place. The smaller line is then threaded down into the jejunum where food or medication delivered; i.e., the gastrojejunostomy line is used to bypass the stomach, delivering nutrition and medication directly into the jejunum.

Because of the smaller size of the gastrojejunostomy tube, only liquids are delivered through such a line. Gastrojejunostomy lines typically have two ports, including one that delivers to the stomach and another that bypasses the stomach directly into the small intestine. When a patient may only receive food and/or medication directly into the jejunum, and the stomach is completely bypassed, the stomach commonly fills with stomach acid, digestive enzymes, and the resulting gas or trapped air. Because the liquids are not diluted and/or expelled into the intestines, as they ordinarily would be, and because of the pressures of gas or trapped air, the patient may be forced to vomit, suffer from acid reflux, or may suffer from other serious esophageal problems.

Thus, a gastrojejunostomy drainage bag solving the aforementioned problems is desired.

SUMMARY

In one aspect of the invention, a gastrojejunostomy tube is used when a patient's stomach must be bypassed, with nutrients and/or medication being delivered directly to the jejunum. In this situation, the stomach commonly fills with stomach acid and digestive enzymes, which may cause vomiting, acid reflux or other esophageal problems. The gastrojejunostomy drainage bag in a dependant portion is provided to allow the contents of the stomach to be drained through the gastrojejunostomy tube rather than building up within the patient's stomach.

The gastrojejunostomy drainage bag includes a receptacle having a lower portion and an upper stem portion, with the upper stem portion terminating in a port adapted for connection to the gastrojejunostomy tube. Preferably, a lower port is formed through the lower portion, allowing the contents of the gastrojejunostomy drainage bag to be selectively emptied.

In another aspect of the invention, the gastrojejunostomy drainage bag is inverted so that trapped air or gas is released from the patient's stomach into the inverted lower portion of the receptacle. The trapped air or gas is released through a valve, relieving the patient's discomfort of gas and trapped air.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION

Figure 1:
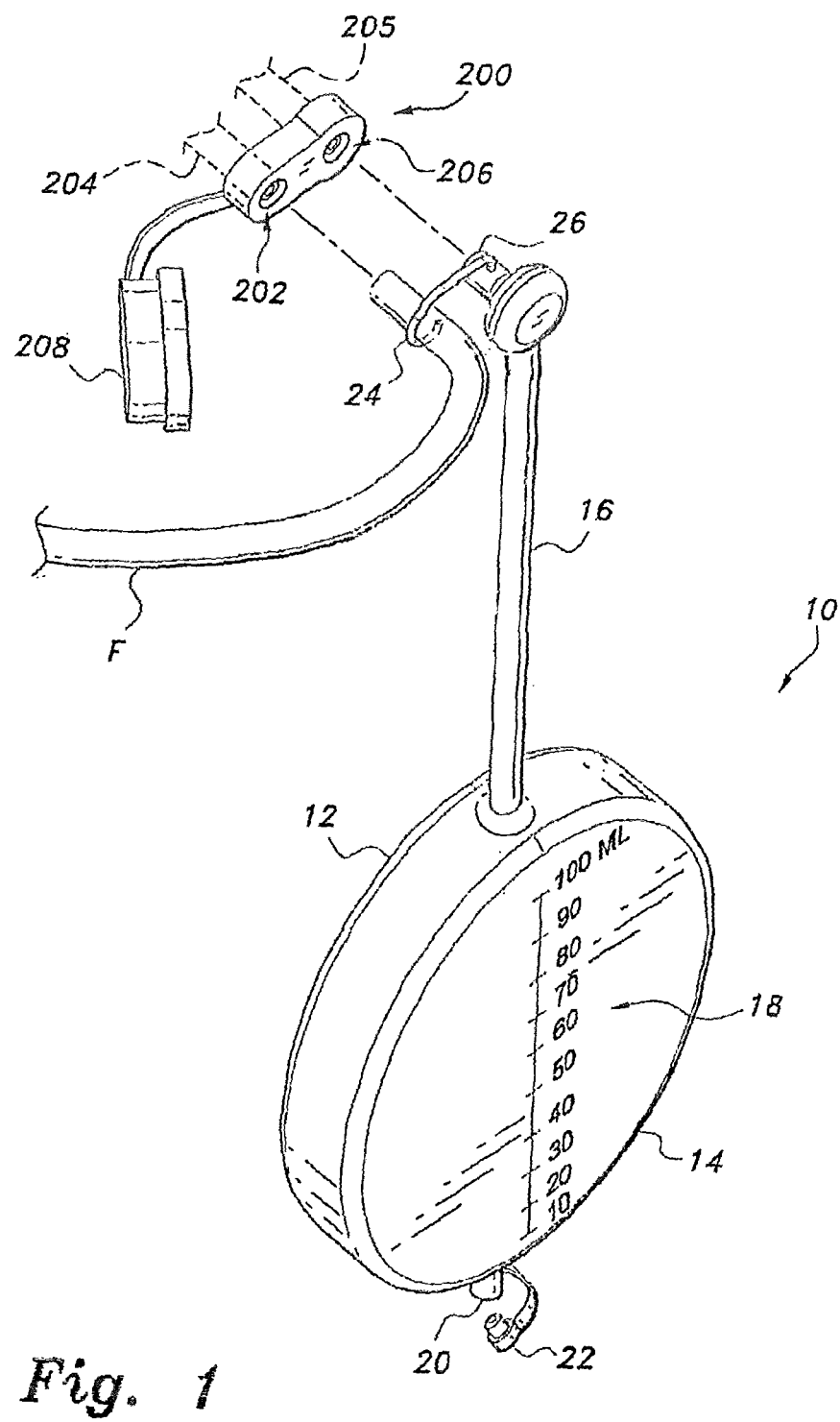
FIG. 1 is a perspective view of a gastrojejunostomy drainage bag according to the present invention.
Figure 2:
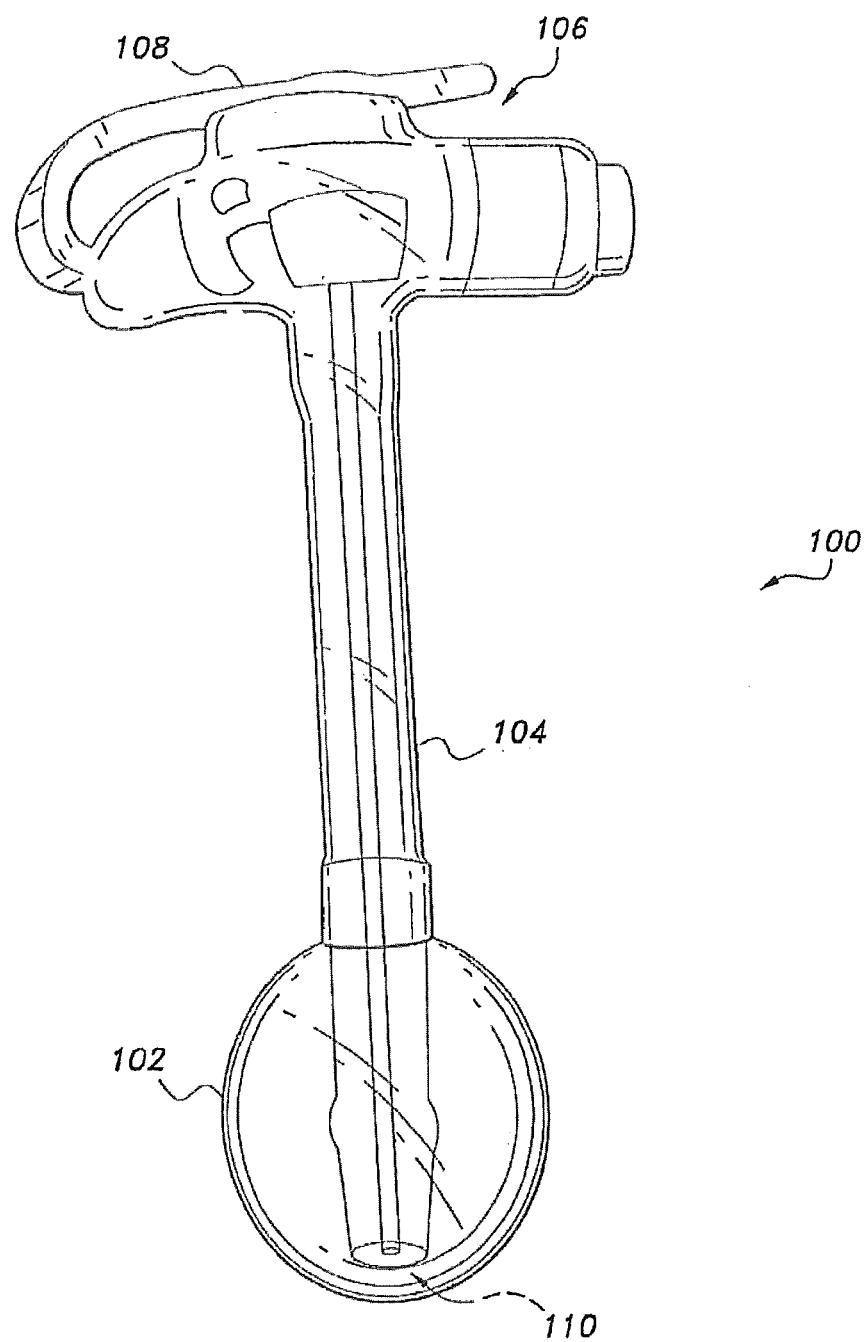
FIG. 2 is a perspective view of a gastrostomy tube according to the prior art.
Figure 3:
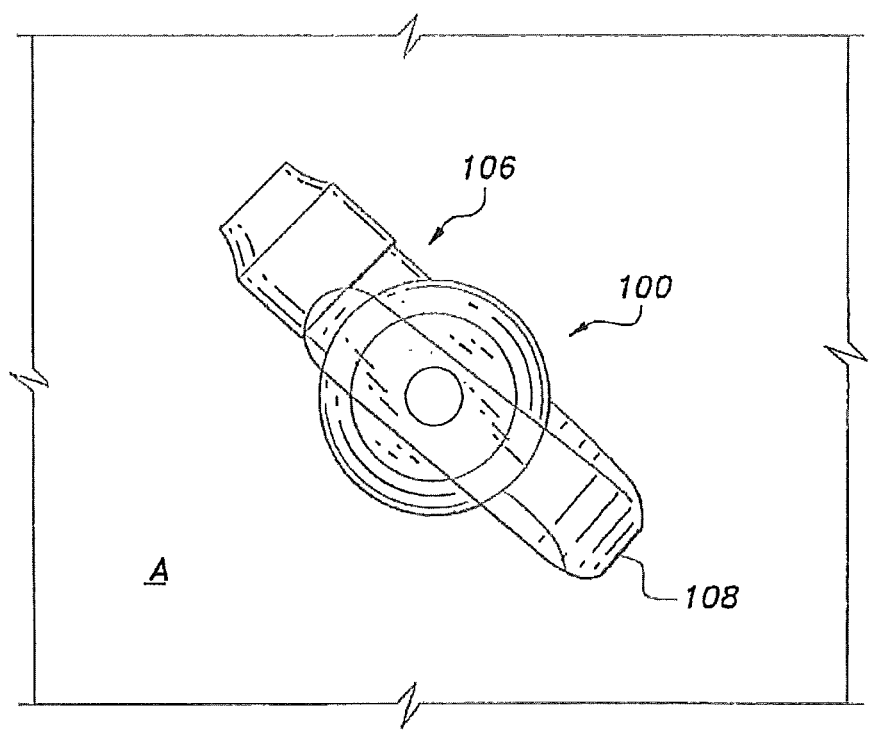
FIG. 3 is a front view of the prior art gastrostomy tube of FIG. 2, shown implanted in a patient.

FIG. 1 partially illustrates a medical device 10 comprising a gastrojejunostomy tube 200, similar to the gastrostomy tube 100 of FIGS. 2 and 3, but specifically adapted to the needs of a gastrojejunostomy, i.e., the gastrojejunostomy tube 200 terminates in a first port 202, which places a first central feeding tube line 204 directly into the patient's pyloric sphincter to the jejunum and also a second port 206, which places second central tube line 205 into the patient's stomach. A cover 208 is provided for covering first and second ports 202, 206. In FIG. 1, an exemplary feeding tube F is shown, adapted for connection to first port 202 for delivery of nutrients and/or medication directly into the patient's jejunum. To prevent reflux and/or vomiting, fundoplication is generally performed surgically during initial placement of central tube line 204, 205.

In the situation where the patient only receives nutrition directly into the jejunum, and the stomach is completely bypassed, the stomach commonly fills with stomach acid and digestive enzymes. Because these are not diluted and/or expelled into the intestines, as they ordinarily would be, the patient may be forced to vomit, suffer from acid reflux, or be subject to other serious esophageal problems. Thus, gastrojejunostomy drainage bag 10 is provided, allowing the contents of the stomach to be drained through second port 206, rather than building up within the patient's stomach.

The gastrojejunostomy drainage bag 10 includes a receptacle 12, formed from medical-grade plastic, for example, polyvinylchloride, polyethylene, polypropylene, or the like (as is well known in the construction of colostomy bags, for example), and includes a substantially bulbous lower portion 14 and an upper stem portion 16. The stem portion 16 terminates in port 26 adapted for connection to second port 206 of the gastrojejunostomy tube 200 and promotes the drainage of gastric secretions or contents of the user's stomach from the stomach into the lower portion 14 of receptacle 12. In order to better align and secure the gastrojejunostomy drainage bag 10 to the gastrojejunostomy tube 200, a hook 24 may be mounted on the upper end of stem portion 16, as shown, for hooking onto the feeding tube F. Additionally, port 26 may be held in place by the further use of medical tape or the like.

An exterior face of lower portion 14 may have indicia 18 formed thereon, which may be in the form of a graduated volume measurement, as shown. Additionally, a lower port 20 is formed through the lower end of the lower portion 14, as shown, for emptying the contents of gastrojejunostomy drainage bag 10. A releasable cover 22 is provided for releasably sealing the lower port 20. The receptacle 12 and lower portion 14 are used in a dependent position, below the patient's stomach, allowing gravity to drain gastric secretions into the lower portion 14 of receptacle 12 that accumulate in the stomach.

In another aspect of the invention, a method of removing trapped air or gas from the stomach by using the medical device 10 is disclosed. When fundoplication is performed during surgical placement of second central feeding line 205 into the patient's stomach to prevent reflux and/or vomiting, trapped air in the stomach cannot escape because of the patient's inability to burp and expel the air. Typically, patients are vented between feedings due to the discomfort of gastric secretions or trapped air. Medical device 10 is used in a method to supply food to the jejunum and discharge gas and trapped air and remove gastric secretions from the stomach. The method comprises the steps of inserting a distal portion (not shown) of a first tube line 204 into the patient's jejunum, inserting a distal portion (not shown) of a second tube line 205 into the patient's stomach with proximal portion (not shown) of central tube line 204 and proximal portion (not shown) of second tube 205 engaging first and second ports 202, 206. This configuration allows fluids to drains through port 206 and stem 16 to receptacle 12 and lower portion 14 with lower port 20, valve 22, and releasable cover 22 for releasing contents of lower portion 14 when it is in a dependent position to ports 202, 206. The gastric secretions flow by gravity into lower portion 14 of receptacle 12 since it is below the patient's stomach. To release gas and trapped air from the patient's stomach, receptacle 12 is rotated upwards and inverted so the gas or trapped air will rise into lower portion 14 of receptacle 12, now placed above ports 202, 206 and the patient's stomach. The gas or trapped air is released from the inverted lower portion 14 by removing releasable cover 22 from lower port 20. After central lines 204 and 205 are placed surgically in the patient's jejunum and stomach, the rotation of lower portion 14 and release of the gas or trapped air therefrom is a convenient operation. To assist the gas or trapped air to exit the stomach into central tube line 205, the stomach or abdomen may be compressed externally to force the trapped air into central tube 205 and into receptacle 12 out lower port 20.

Medical device 10 is easily attached to the patient and can be worn under clothing. The patient can readily invert lower portion 14 and release gas or trapped air through lower port when necessary.

It is to be understood that the present invention is not limited to the embodiments described above, but encompasses any and all embodiments within the scope of the following claims.

What is claimed is:

1. A method of releasing gas from a stomach of a patient using a gastrojejunostomy drainage device, the method comprising:
   providing a gastrojejunostomy drainage device comprising a first central tube and a second central tube securable, respectively, to a first port and a second port coverable by a first cover; a feeding tube connectable at a distal end to the first port; a rotatable port connectable at a proximal end to the second port and rotatably connected at a distal end to a drain stem connected at a distal end to a receptacle comprising a lower portion comprising a lower port and a releasable second cover configured for releasably sealing the lower port; and a connector connecting a proximal end of the rotatable port to the distal end of the feeding tube, the connector configured to hold in place the rotatable port;
   inserting a distal end of the first central tube into a jejunum of the patient, the first central tube configured for connection to the feeding tube;
   inserting a distal end of the second central tube into the stomach of the patient, the second central tube configured for draining fluid and gas from the stomach of the patient;
   securing the first port to a proximal end of the first central tube,
   securing the second port to a proximal end of the second central tube and to the proximal end of the rotatable port that is rotatably connected to the proximal end of the drain stem, the receptacle in fluid communication with the distal end of the drain stem, wherein the receptacle is configured to be rotatable relative to the rotatable port from a first dependent position below the rotatable port, the stomach and the second port; to (ii) a second inverted position above the rotatable port, the stomach and the second port;
   connecting the distal end of the feeding tube to the proximal end of the rotatable port with the connector, such that the connector holds in place the rotatable port;
   in the first, dependent, position, allowing fluid and gas to flow from the stomach to the receptacle, wherein the lower port is in a first, sealed, configuration by said second lower cover;
   thereafter rotating and inverting the receptacle relative to the rotatable port to achieve the second, inverted, position;
   thereafter unsealing the second lower cover from the lower port to provide the lower port in a second, unsealed, configuration that releases gas from the inverted lower portion of the receptacle,
   thereafter sealing the second lower cover to the lower port to provide the first, sealed, configuration; and
   thereafter inverting and rotating the receptacle relative to the rotatable port to the first, dependent, position;
   wherein the rotation and inverting of the receptacle relative to the rotatable port, (a) between the first, dependent, position and the second, inverted, position; or
   (b) between the second, inverted, position and the first, dependent, position; is independent of the connector connecting the rotatable port and the distal end of the feeding tube, and holding in place the rotatable port, without rotation or inversion of the feeding tube.

2. The method of claim 1, wherein the first port further includes the connector as a hook configured to secure the first port to a feeding tube.

3. The method of claim 1, wherein the receptacle further includes graduated volume measurement indicia.

4. The method of claim 1, wherein the receptacle comprises a medical-grade plastic.

5. The method of claim 4, wherein the medical-grade plastic is selected from polyvinylchloride, polyethylene, and polypropylene.

6. The method of claim 1, wherein the method further comprises placing the gastrojejunostomy drainage device underneath the clothing of the patient.

7. The method of claim 1, wherein the receptacle includes a substantially round first wall, a substantially round second wall opposite first wall, and a side wall connecting the first wall and the second wall substantially about the circumferences of the first wall and the second wall.

8. The method of claim 7, wherein the receptacle is formed of a rigid or semi-rigid material.

9. The method of claim 7, wherein the stem portion is attached to the receptacle through the side wall.

10. The method of claim 7, wherein the side wall comprises the lower port.

11. The method of claim 7, wherein the stem portion is attached to the receptacle through the side wall, and wherein the lower port is attached to the side wall substantially opposite the stem portion.

12. The method of claim 1 further comprising:
adjusting the lower port while the receptacle is not in the second inverted and rotated position to provide a third, unsealed configuration; and
thereafter releasing fluid from the gastrojejunostomy device through the lower port.

13. The method of claim 12, wherein the step of releasing fluid through the lower port is performed before the step of rotating and inverting the receptacle relative to the rotatable port.

14. The method of claim 12, wherein the step of releasing fluid through the lower port is performed after the step of inverting and rotating the receptacle relative to the rotatable port to return the receptacle to the first, dependent position.

15. The method of claim 1, wherein the patient has previously had fundoplication surgery.

16. A method of enabling a patient in which a gastrojejunostomy tube has been implanted to release gas from the patient's stomach, the method comprising:
providing the patient with a portable, wearable gastrojejunostomy drainage device comprising a first central tube and a second central tube securable, respectively, to a first port and a second port coverable by a first cover; a feeding tube connectable at a distal end to the first port; a rotatable port connectable at a proximal end to the second port and rotatably connected at a distal end to a drain stem connected at a distal end to a receptacle comprising a lower portion comprising a lower port and a releasable second cover configured for releasably sealing the lower port; and a connector connecting a proximal end of the rotatable port to the distal end of the feeding tube, the connector configured to hold in place the rotatable port;
inserting a distal end of the first central tube into a jejunum of the patient, the first central tube configured for connection to the feeding tube;
inserting a distal end of the second central tube into the stomach of the patient, the second central tube configured for draining fluid and gas from the stomach of the patient;
securing the first port to a proximal end of the first central tube,
securing the second port to a proximal end of the second central tube and to the proximal end of the port rotatably connected to the proximal end of the stem portion, the receptacle in fluid communication with the distal end of the stem portion, wherein the receptacle is configured to be rotatable relative to the rotatable port from (i) a first, dependent, position below the rotatable port, the stomach and the second port; to (ii) a second, inverted, position above the rotatable port, the stomach and the second port;
connecting the distal end of the feeding tube to the proximal end of the rotatable port with the connector, such that the connector holds in place the rotatable port;
in the first, dependent, position, allowing fluid and gas to flow from the stomach to the receptacle, wherein the lower port is in a first, sealed, configuration by said second lower cover;
thereafter rotating and inverting the receptacle relative to the rotatable port to achieve the second, inverted, position;
thereafter unsealing the second lower cover from the lower port to provide the lower port in a second, unsealed, configuration that releases gas from the inverted lower portion of the receptacle,
thereafter sealing the second lower cover to the lower port to provide the first, sealed, configuration; and
thereafter inverting and rotating the receptacle relative to the rotatable port to the first, dependent, position;
wherein the rotation and inverting of the receptacle, relative to the rotatable port, (a) between the first, dependent, position and the second, inverted, position; or (b) between the second, inverted, position and the first, dependent, position;
is independent of the connector connecting the rotatable port and the distal end of the feeding tube and holding in place the rotatable port, without rotation or inversion of the feeding tube; and
wherein the patient has previously had fundoplication surgery.

17. The method of claim 16, wherein the receptacle is formed of a rigid or semi-rigid material.

* * * * *